United States Patent [19]

Sawa et al.

[11] Patent Number: 4,826,991

[45] Date of Patent: May 2, 1989

[54] PRODUCTION OF 1-AMINOETHYL-IMIDAZOLES VIA THE HYDROLYSIS OF 1-ACYLAMINOETHYLIMIDAZOLES

[75] Inventors: Natsuo Sawa, Tadotsu; Takeshi Masuda, Marugame; Takayuki Murai, Tadotsu; Singi Okazaki; Yukio Miyauchi, both of Marugame; Masayuki Ito, Sakado, all of Japan

[73] Assignee: Shikoku Chemicals Corporation, Kagawa, Japan

[21] Appl. No.: 16,771

[22] Filed: Feb. 20, 1987

[30] Foreign Application Priority Data

Feb. 24, 1986 [JP] Japan .................................. 61-39723

[51] Int. Cl.$^4$ ..................... C08G 59/44; C08G 59/50; C07D 233/54
[52] U.S. Cl. ..................... 548/341; 548/352; 528/94; 528/117
[58] Field of Search ................................ 548/341, 352

[56] References Cited

U.S. PATENT DOCUMENTS

| | | | |
|---|---|---|---|
| 3,489,695 | 1/1970 | Green | 528/117 |
| 3,531,494 | 9/1970 | Adolphi | 548/341 |
| 3,592,826 | 7/1971 | Marcus | 548/335 |

FOREIGN PATENT DOCUMENTS 2126225A  3/1984  United Kingdom ................ 548/341

OTHER PUBLICATIONS

Chem Abstract 95(23): 203822d.
Chem Abstract 94(2): 4941w.
Chem Abstract 94(3): 14484p.

*Primary Examiner*—Earl Nielsen
*Assistant Examiner*—Frederick Krass
*Attorney, Agent, or Firm*—Sherman & Shalloway

[57] ABSTRACT

An imidazole compound represented by the general formula

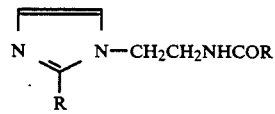

wherein R is an alkyl group having up to 17 carbon atoms or a phenyl group. This imidazole compound is useful as a curing agent or curing accelerator for epoxy resins.

2 Claims, No Drawings

PRODUCTION OF 1-AMINOETHYL-IMIDAZOLES VIA THE HYDROLYSIS OF 1-ACYLAMINOETHYLIMIDAZOLES

BACKGROUND OF THE INVENTION (1) Field of the Invention

This invention relates to novel imidazole compounds, a process for synthesizing these compounds, and a method of curing epoxy resins using these compounds.

The compounds obtained by this invention are novel, and useful as a curing agent or a curing accelerator for epoxy resins.

(2) Description of the Prior Art

Nowadays, various imidazole compounds are used as curing agents or curing accelerators in the epoxy resin industry. Among them, 2-ethyl-4-methylimidazole (2E4MZ for short) is by far most frequently used throughout the world.

2E4MZ is intrinsically a normally crystalline substance having a melting point of about 45° C. After it is purified by distillation under reduced pressure, it is liquid at ordinary temperature for a considerably long period of time owing to an overcooling phenomenon. Such liquid 2E4MZ has excellent compatibility with liquid epoxy resins, and this is presumably one reason why it finds worldwise extensive use. However, since it is crystalline at ordinary temperatures, breaking of the overcooling phenomenon by some cause results in its solidification. At least the following empirical knowledge exists with regard to the cause of breaking overcooling.

It is known that a crystal nucleus sometimes forms in liquid 2E4MZ when a certain physical stimulation (for example, vigorous vibration or rubbing of the inside surface of the container by a pointed solid object) is given to it or a certain minute foreign material is included in it, and that once the crystal nucleus forms, crystals grow from it and soon the entire 2E4MZ solidifies. It is also known that liquid 2E4MZ entirely solidifies almost surely when the crystals of 2E4MZ are finely pulverized and added to liquid 2E4MZ (so-called nucleation).

When liquid 2E4MZ solidifies, its compatibility with a liquid epoxy resin is naturally inferior to that of liquid 2E4MZ. The solidified 2E4MZ becomes liquid when melted by heating. This, however, is troublesome, and the user dislikes the solidification.

2E4MZ is now commercially available in various purities. The ease or difficulty of its solidification depends upon its purity. Generally, solidification is easier for higher purities, and more difficult for lower purities. The present applicants are manufacturing and selling 2E4MZ, which are purified by distillation under reduced pressure and supply to the industry relatively high-purity grades having an average purity of 97% and a Gardner number of 2 to 3. They are however liable to solidify, and particularly in the wintertime, there is a tendency to accelerated solidification. 2E4MZ manufactured by a certain company in West Germany has an average purity of as high as 97%, and therefore readily solidifies.

In contrast, 2E4MZ manufactured by a certain company in U.S.A. has a purity of as low as 82% and contains considerable amounts of impurities. Its color hue is expressed by a Gardner number of at least 18 (scale out). Hence, this 2E4MZ is difficult of solidification, but because of its low purity, it often fails to attract the user's interest.

No product which has a high purity and does not solidify is found among 2E4MZ products now commercially available.

Users who dislike solidification must equip themselves with a device for keeping 2E4MZ warm to maintain it liquid. Although there is a strong demand in the industry for the advent of 2E4MZ which does not solidify, the advent of such 2E4MZ is impossible judging from its inherent property. In short, the industry has sought a method of solving a problem which is impossible of solution.

Extensive investigations of the present inventors have led to the discovery that a certain class of 1-aminoethylimidazole compounds are liquid, and that these compounds have properties equivalent to 2E4MZ as curing agents or curing accelerators for epoxy resins. The problems associated with 2E4MZ are solved by the provision of 1-aminoethyl-imidazole compounds of the invention.

Means of solving these problems will now be described.

First, a method of synthesizing a 1-acylaminoethyl-imidazoline compound which becomes a starting material for the 1-aminoethyl-imidazole compound will be described.

This synthesis is carried out by any one of the following two methods using diethylenetriamine (DETA for short).

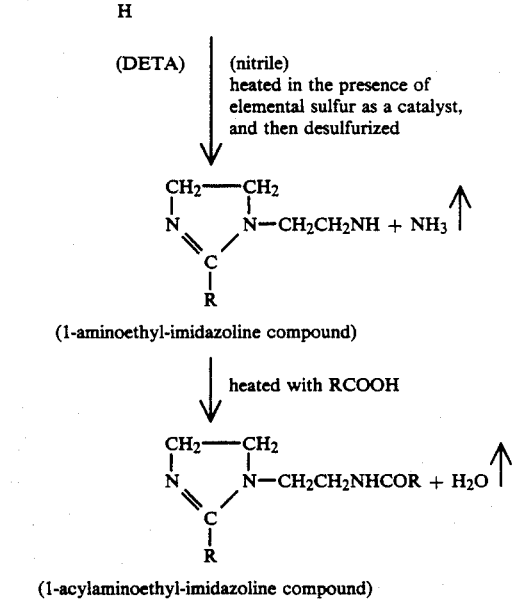

In the above reaction, RCN and RCOOH are used each in an amount of 1 to 1.2 moles per mole of DETA. Desulfurization of the 1-aminoethyl-imidazoline compound is carried out by heating the reaction mixture with an alkali hydroxide, zinc dust or iron dust, filtering the heated mixture, and distilling the filtrate under reduced pressure or recrystallizing it. The reaction of the desulfurized 1-aminoethyl-imidazoline compound with RCOOH is carried out while evaporating the water formed. When the evaporation ceases, the reaction mixture is subjected to dehydrogenation.

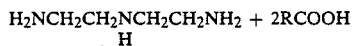

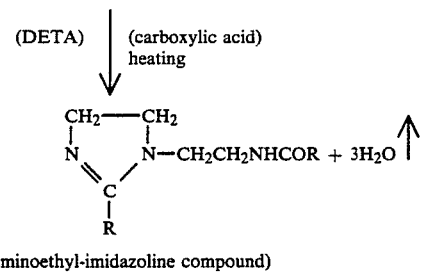

(1-acylaminoethyl-imidazoline compound)

In method (2), 2 to 2.4 moles of RCOOH or 1 to 1.2 moles of RCO O COR (acid anhydride) is used per mole of DETA.

The reaction is carried out while evaporating the water formed. When the evaporation ceases, the resulting mixture is subjected to dehydrogenation.

The present inventors found that the 1-aminoethyl-imidazoline compound, a precursor of the 1-acylamino-ethyl-imidazoline compound in method (1) does not undergo dehydrogenation in the presence of the catalyst used in this invention. Extensive investigations have led to the discovery that the dehydrogenation reaction proceeds if it is acylated to a 1-acylaminoethyl-imidazo-line compound. This discovery has led to the present invention.

Then, 1-acylaminoethyl-imidazoline compound is heated together with a metal catalyst (Group VIII of the periodic table) at a temperature of 150° to 270° C. whereby it is dehydrogenated to a 1-acylaminoethyl-imidazole compound. This is schematically shown as follows.

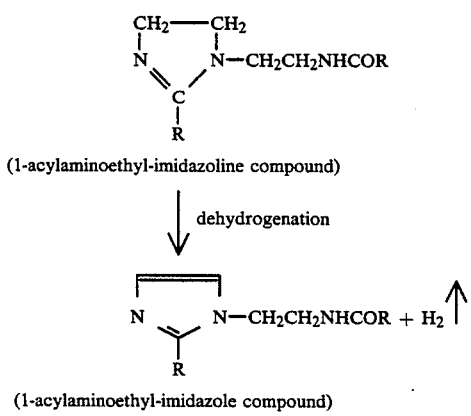

Ni, Co, Pd and Pt can be used as the metal catalyst. In view of economy, Ni is most preferably used. Particularly, the use of commercially available stabilized nickel (a product of Nikki Chemical Co., Ltd.) is preferred. The stabilized nickel is used in an amount of 5 to 10% by weight based on the imidazoline compound.

The dehydrogenation usually ends within 1 hour. The dehydrogenation reaction mixture is filtered, and the metal catalyst is separated by filtration and recovered. The filtrate is subjected to distillation under reduced pressure or to recrystallization to obtain the 1-acylaminoethyl-imidazole compound. The 1-acylaminoethyl-imidazole compound is important as a precursor of a 1-aminoethyl-imidazole compound.

The resulting 1-acylaminoethyl-imidazole compound is a novel substance. Hydrolysis and subsequent purification in a customary manner give the final desired 1-aminoethyl-imidazole compound.

Hydrolysis is carried out using an alkali hydroxide or sulfuric acid. As a solvent for this reaction, there may be used water, hydrous ethylene glycol, hydrous diethylene glycol or hydrous methyl Cellosolve R (monomethoxyethylene glycol). Most of the 1-aminoethyl-imidazole compounds obtained by the above procedure are liquid and novel compounds. They are useful as curing agents or curing accelerators for epoxy resins.

The properties of the compounds of this invention are shown below.

1-Acetylaminoethyl-2-methylimidazole

Basic colorless crystals; m.p. 125°–128° C. (acetone); soluble in water, methanol and acetic acid; TLC (silica G, EtOH, Iz); Rf 0.20–0.46.

| $\nu_{cm-1}^{KBr}$: | 3430(53),3220(38),3138(37),3118(39) |
|---|---|
| | 3060(35),2960(38),2862(51),1668(12) |
| | 1568(32),1530(42),1530(43),1501(34) |
| | 1468(45),1425(37),1372(37),1306(40) |
| | 1288(35),1265(42),1244(57),1163(63) |
| | 1143(57),1120(66),1093(50),1053(71) |
| | 1037(70),982(46),925(71),912(75) |
| | 865(77),838(75),770(46),701(71) |
| | 677(51) |

The figures in the parentheses show transmittances (%). (The same applies hereinafter.)

NMR(CFPV$_3$COOH): δ 7.82, br, t, 1H; 7.32, S, 2H; 4.41, t, 2H; 3.88 q, 2H; 2.76, S, 3H; 2.23, S, 3H.

Mass: m/e 168, 167 (M+), 152, 124, 109, 108, 107, 97, 96, 95, 86, 83, 82, 81, 72, 68, 55, 54, 44, 43, 42, 41.

1-Aminoethyl-2-methylimidazole

Basic colorless liquid; bp$_{760}$ 275°–278° C.; easily soluble in water, methanol, ethanol, acetone and toluene, TLC (silica G, EtOH, Iz): Rf 0.05–0.28.

| $\nu_{cm-1}^{liquid\ film}$: | 3360(35),3280(36),3110(49),2940(51) |
|---|---|
| | 2870(61),1595(61),1520(52),1500(38) |
| | 1465(54),1423(30),1358(64),1273(35) |
| | 1140(62),1086(71),1070(72),1035(72) |
| | 980(55),920(60),845(55),730(43) |
| | 668(39) |

1-Aminoethyl-2-methylimidazole oxalate

Weakly acidic colorless crystals; m.p. 184°–185° C. (water-methanol).

NMR(D$_2$O) δ 7.43, d (J=2 Hz), 1H; 7.36, d (J=2 Hz), 1H; 4.48, t (J=7 Hz), 2H; 3.50, t (J=7 Hz), 2H; 2.64, S, 3H.

Mass: m/e 125 (M), 96, 95, 81, 68, 55, 54, 46, 45, 42.

1-Propionylaminoethyl-2-ethylimidazole

Basic colorless liquid; bp$_{11}$ 224°–227° C.; easily soluble in water, methanol, ethanol and chloroform; TLC (silica G, EtOH, Iz): Rf 0.44–0.57.

| $\nu_{cm-1}^{liquid\ film}$: | 3270(17),3050(23),2970(17),2940(19) |
|---|---|
| | 1655(21),1545(25),1490(27),1460(29) |
| | 1430(29),1370(36),1272(34),1230(36) |
| | 1156(49),1136(53),1080(55),1058(46) |
| | 1036(45),920(64),878(67),830(67) |

-continued

714(43)

NMR(CDCl₃): δ 7.52, br.t, 1H; 6.77, S, 2H; 4.00, t (J=5.6 Hz), 2H; 3.48, q (J=5.6 Hz) 2H; 2.61, q (J=7.6 Hz), 2H; 2.21, q (J=7.6 Hz), 2H; 1.26, t, (J=7.6 Hz), 3H; 1.13, t (J=7.6 Hz), 3H.

Mass: m/e 195 (M+), 166, 138, 123, 121, 109, 107, 97, 95, 81, 69, 58.

1-Aminoethyl-2-ethylimidazole

Basic liquid; bp₁₀ 145°–149° C.; easily soluble in water, ethanol and chloroform.

1-Aminoethyl-2-ethylimidazole picrate m.p. 225° C. (decomp.) (water); TLC (silica G, EtOH): Rf 0.0–0.07 (color formation with ninhydrin), 0.71–0.77 (picric acid, yellow spot).

| $\nu_{cm-1}^{KBr}$: | 3430(68),3050(46),2900(43),2780(45) |
|---|---|
| | 1626(22),1604(12),1562(15),1533(19) |
| | 1510(20),1480(32),1430(37),1356(15) |
| | 1320(14),1280(24),1265(20),1554(43) |
| | 1074(42),964(63),933(64),910(57) |
| | 900(50),880(57),845(60),830(66) |
| | 780(55),758(52),734(55),700(39) |
| | 685(54) |

NMR(DMSO-d₆): δ 8.57, S, 4H; 7.88, br.3H; 7.62, S, 2H; 4.32, t (J=6.4 Hz), 2H; 3.30, br.t.3H; 2.95, q (J=7.6 Hz) 2H; 1.28, t (J=7.6 Hz), 3H.

Mass: m/e 229, 213, 199, 171, 155, 152, 139 (M+), 110, 109, 91, 80, 62, 53, 50.

1-iso-Butyrylaminoethyl2-isopropylimidazole

Basic colorless liquid; bp₂₀ 222°–224° C.; TLC (silica G, EtOH, Iz color formation): RF 0.50–0.58.

| $\nu_{cm-1}^{liquid\ film}$: | 3300(31),2975(29),2935(33),2875(39) |
|---|---|
| | 1653(32),1550(39),1490(41),1469(42) |
| | 1444(45),1380(52),1360(50),1270(53) |
| | 1240(50),1176(58),1152(67),1123(63) |
| | 1087(49),1068(48),1042(48),959(75) |
| | 925(70),876(67),850(68),716(51) |

NMR(CD₃OD) δ 6.93, d (J=1 Hz), 1H; 6.83, d (J=1 Hz), 1H; 4.06, t (J=6 Hz), 2H; 3.42, t (J=6 Hz), 2H; 3.3–2.9, m, 1H; 2.6–2.2, m, 1H; 1.27, d (J=7 Hz), 6H; 1.06, d (J=7 Hz), 6H.

Mass: m/e 223 (M+) 136, 121, 114, 111, 109, 95, 43.

1-Aminoethyl-2-isopropylimidazole

Basic colorless liquid; bp₂₀ 130°–139° C.; TLC (silica G, EtOH, Iz): RF 0.20–0.40.

| $\nu_{cm-1}^{liquid\ film}$: | 3360(44),3280(39),3100(50),2965(15) |
|---|---|
| | 2925(25),2865(34),1600(57),1515(55) |
| | 1485(20),1465(31),1435(33),1378(53) |
| | 1358(49),1325(57),1269(24),1150(47) |
| | 1095(50),1064(29),1035(58),919(52) |
| | 834(48),740(44),717(28) |

NMR(CD₃OD) δ 6.97, d (J=1 Hz), 1H; 6.84 d (J=1 Hz), 1H; 3.99, t (J=7 Hz), 2H; 3.2–3.0, m, 1H; 2.91, t (J=7 Hz), 2H; 1.27, d (J=7 Hz), 6H.

Mass: me 153 (M+), 124, 123, 111, 109, 108, 107, 96, 95, 81, 69, 54, 42.

1-Lauroylaminoethyl-2-undecylimidazole

Basic colorless crystals; m.p. 56°–59° C. (methanol); soluble in hot methanol, hot dimethyl sulfoxide, and chloroform; TLC (silica G, EtOH, Iz): RF 0.76–0.85.

| $\nu_{cm-1}^{KBr}$: | 3320(22),2960(27),2920(6),2855(13) |
|---|---|
| | 1650(14),1552(35),1485(60),1470(28) |
| | 1440(66),1425(65),1413(59),1375(65) |
| | 1364(68),1300(78),1275(68),1245(73) |
| | 1222(75),1193(81),1159(75),1145(82) |
| | 1086(82),1050(91),950(90),925(90) |
| | 905(90),865(89),754(74),744(74) |
| | 712(62),672(80) |

NMR(CDCl₃) δ 6.90, d (J=1.6 Hz), 1H; 6.75, d (J=1.6 Hz), 1H; 5.94, br.t.1H; 3.99, t (J=6 Hz), 2H; 3.49, q (J=6 Hz), 2H; 2.59, t (J=8 Hz), 2H; 2.16, t (J=9 Hz), 2H; 1.60, br.m, 4H; 1.24, S, 32H: 0.87, t (J=6 Hz), 6H.

Mass: m/e 448, 447 (M+), 386, 368, 354, 293, 278, 256, 228, 201, 185, 167, 149, 137, 129, 115, 109, 97, 83, 69, 57, 43.

1-Aminoethyl-2-undecylimidazole

Basic colorless liquid; easily soluble in methanol, ethanol and chloroform; insoluble in water; TLC (silica G, EtOH, Iz): Rf 0.08–0.23

| $\nu_{cm-1}^{liquid\ film}$: | 3370(27),3290(27),3110(31),2920(16) |
|---|---|
| | 2850(17),1595(34),1517(36),1490(22) |
| | 1460(20),1426(22),1374(36),1354(36) |
| | 1274(23),1150(44),1090(39),920(41) |
| | 830(37),716(27),661(40) |

NMR(CD₃OD): δ 6.98, d (J=0.8 Hz), 1H; 6.82, d (J=0.8 Hz), 1H; 3.95, t (J=6.4 Hz), 2H; 2.90, t (J=6.4 Hz), 2H; 2.69, t (J=8.0 Hz), 2H; 1.66, br.m, 2H; 1.26, S, 16H; 0.88, br.t, 3H.

Mass: m/e 265 (M+), 236, 223, 208, 194, 180, 165, 151, 138, 125, 123, 109, 96, 95, 83, 55, 43.

1-Aminoethyl-2-undecylimidazole sulfate

Weakly acidic colorless crystals; m.p. 156°–158° C. (methanol).

| $\nu_{cm-1}^{KBr}$: | 3420(33),3030(21),2955(16),2920(7) |
|---|---|
| | 2850(13),1716(21),1700(21),1630(15) |
| | 1604(14),1515(21),1470(20),1445(19) |
| | 1402(18),1330(35),1275(21),1210(17) |
| | 1150(20),1100(22),950(32),940(32) |
| | 905(37),865(42),790(47),754(41) |
| | 714(14) |

1-Stearoylaminoethyl-2-heptadecylimidazole

Weakly basic pale yellow crystals; m.p. 76°–82° C. (methanol); easily soluble in chloroform and hot methanol; sparingly soluble in methanol and acetone; TLC (silica G, MeOH, color formation with B.T.B): Rf 0.0–0.3.

| $\nu_{cm-1}^{KBr}$: | 3320(41),2960(39),2920(14),2855(21) |
|---|---|
| | 1650(35),1552(48),1485(59),1470(36) |
| | 1425(58),1413(62),1375(64),1360(66) |
| | 1275(65),1258(68),1240(70),1222(68) |
| | 1203(72),1182(74)1158(68),1145(72) |

-continued

1082(70),712(56)

NMR(CDCl₃) δ 6.90, S, 1H; 6.74, S, 1H; 5.98–5.76, br, 1H; 4.00, t (J=7 Hz), 2H; 3.54, t (J=7 Hz), 2H; 2.60, t (J=7 Hz), 2H; 2.14, t (J=7 Hz), 2H; 1.78–1.47, br, 4H; 1.24, S, 56H; 0.87, t, 6H.

Mass: m/e 616 (M+), 587, 573, 559, 545, 531, 517, 503, 489, 475, 461, 477, 433, 419, 405, 392, 377, 333, 307, 305, 267, 239, 109, 82, 57, 43.

1-Aminoethyl-2-heptadecylimidazole

Basic colorless crystals; m.p. 38°–40° C.; easily soluble in methanol, acetone, chloroform and hot water; TLC (silica G, MeOH, color formation with ninhydrin): Rf 0.35–0.45.

| $v^{KBr}_{cm-1}$: | 3350(47),2918(17),2845(22),1595(66) |
| --- | --- |
| | 1515(70),1485(56),1462(43),1420(63) |
| | 1370(75),1350(74),1270(65),1142(79) |
| | 1080(78),1030(84),915(75),875(77) |
| | 845(76),708(63) |

NMR(CDCl₃): δ 6.94, d (J=1 Hz), 1H; 6.84, d (J=1 Hz), 1H; 3.90, t (J=6 Hz), 2H; 3.02, t (J=6 Hz), 2H; 2.66, t (J=7 Hz), 2H; 1.84–1.60, br, 2H; 1.22, S, 28H; 0.88, t, 3H.

Mass: m/e 350 (M++1), 349 (M+), 307, 305, 292, 278, 250, 236, 222, 208, 194, 180, 166, 152, 138, 125, 109, 96, 83, 57, 55, 43, 41.

1-Benzoylaminoethyl-2-phenylimidazole

Colorless neutral crystals; m.p. 132°–135° C. (ethylene glycol); easily soluble in methanol, ethanol and acetone; insoluble in hot water; TLC (silica G, EtOH, Iz): Rf 0.75–0.90.

| $v^{KBr}_{cm-1}$: | 3240(22),3070(28),2940(36),1975(71) |
| --- | --- |
| | 1900(73),1820(73),1770(75),1645(4) |
| | 1600(26),1575(22),1550(8),1490(23) |
| | 1460(19),1435(25),1410(15),1345(32) |
| | 1320(29),1300(10),1280(17),1260(12) |
| | 1175(46),1145(43),1080(28),1025(55) |
| | 1010(56),955(34),910(51),855(61) |
| | 845(63),800(64),765(13),745(34) |
| | 720(31),690(9) |

NMR(CDCl₃): δ 7.20–7.70, m, 10H; 7.06, t, 1H; 7.00, d, 1H; 6.95, d, 1H; 4.24, t, 2H; 3.58, q, 2H.

Mass: m/e 292, 291, 171, 170, 157, 148, 105, 77.

1-Aminoethyl-2-phenylimidazole

Basic colorless crystals; mp. ca. 30° C., bp₂₀ 162°–196° C.; TLC (silica, G, EtOH, Iz): Rf 0.10–0.25.

| $v^{liquid\,film}_{cm-1}$: | 3360(30),3270(30),3090(34),3060(35) |
| --- | --- |
| | 2930(29),1770(55),1600(38),1490(23) |
| | 1465(14),1435(20),1410(16),1360(50) |
| | 1265(16),1120(37),1065(32),1010(33) |
| | 905(33),840(41),765(15),735(30) |
| | 705(17),690(16) |

1-Aminoethyl-2-phenylimidazole hydrochloride

Acidic colorless crystals; m.p. >250° C.; soluble in water and methanol; TLC (silica G, EtOH, Iz): Rf 0.0–0.20 (HCl), 0.20–0.40 (base).

| $v^{KBr}_{cm-1}$: | 2780(16),2720(21),2600(29),1605(42) |
| --- | --- |
| | 1585(35),1490(31),1425(48),1400(60) |
| | 1373(55),1350(57),1330(53),1105(53) |
| | 1040(71),1007(73),960(64),913(66) |
| | 878(46),768(33),710(38),690(52) |
| | 685(49) |

NMR(D₂O): δ 7.72, m, 6H; 7.63, d, 1H; 4.64, t, 2H; 3.46, t, 2H.

Mass: m/e 188 (M++1), 187 (M+), 158, 157, 145, 130 104, 103, 89, 77, 63, 52.

The epoxy resin used in this invention has more than one epoxy group on an average per molecule. The epoxy groups may be situated at the ends of a molecule, or in its intermediate. The epoxy resin may be aliphatic, alicyclic or aromatic.

Most desirably used epoxy resins are polyglycidyl ethers of bisphenol A, bisphenol F, resorcinol, diphenol, a phenol/formaldehyde condensate and a cresol/formaldehyde condensate.

The 1-aminoethylimidazole compound in accordance with this invention may be incorporated in an amount of 0.2 to 23% by weight based on the epoxy resin as a curing agent or a curing accelerator.

The method of this invention may be applied to a mixture comprising the epoxy resin and as required, a pigment, a plasticizer, a filler, etc.

The following Examples illustrate the present invention more specifically.

EXAMPLE 1

DETA (0.1 mole; 10.3 g) and 0.2 mole (12.0 g) of acetic acid were heated in a Claisen flask while evaporating the water formed. In 1.5 hours, the evaporation ceased and the inside temperature finally reached about 250° C. Then, a gas sealer as fitted to the flask, and 5% by weight (1.1 g), based on the weight of the starting materials charged, of stabilized nickel was added to the reaction mixture, and the mixture was heated at an inside temperature of about 250° C. for 10 minutes.

During this period, continuous evolution of hydrogen was observed. After the evolution of hydrogen ceased, about 30 ml of methanol was added to the reaction mixture, and the stabilized nickel was separated by filtration. The filtrate was distilled under reduced pressure to give 0.087 mole (14.5 g; yield 87 mole % based on DETA) of a crude 1-acetylaminoethyl-2-methylimidazole fraction having a bp₂₀ of 220° to 232° C.

The crude 1-acetylaminoethyl-2-methylimidazole (0.1 mole; 16.7 g) obtained as above, 0.15 mole (6.0 g) of NaOH and 16 ml of water were heated under reflux for 3 hours. Carbon dioxide gas was blown into the reaction mixture fully, and then the reaction mixture was concentrated under reduced pressure. The concentrate was extracted with ethanol, and the extract was distilled under reduced pressure to give 0.074 mole (9.3 g, yield 74 mol %) of a crude 1-aminoethyl-2-methylimidazole fraction (bp₂₀ 129°–135° C.).

EXAMPLE 2

DETA (0.1 mole; 10.3 g), 0.1 mole (4.1 g) of acetonitrile and 0.2 g of sulfur were heated in a reactor equipped with a bubble counter and a reflux condenser until continuous evolution of ammonia gas ceased. In 2 hours, the evolution of ammonia gas ceased, and the inside temperature finally reached about 220° C. The reaction mixture was then distilled under reduced pressure. Zinc dust (0.8 g) was added to the resulting distillate, and the mixture was heated with stirring at an inside temperature of 240° C. for 2 hours. The reaction mixture was extracted with methanol, and the extract was distilled under reduced pressure to give 0.082 mole (10.4 g; yield 82 mole % based on DETA) of a crude 1-aminoethyl-2-methylimidazoline fraction having a $bp_{20}$ of 150°–155° C.

The resulting crude imidazoline (0.05 mole; 6.4 g) and 0.05 mole (3.0 g) of acetic acid were heated in a Claisen flask while evaporating the water formed. In 1 hour, the evaporation ceased, and the inside temperature finally reached about 250° C. During this time, 0.5 ml of water distilled out. A bubble counter was fitted to the flask, and 5% by weight (0.5 g), based on the weight of the starting materials charged, of stabilized nickel was added to the reaction mixture obtained as above. The mixture was heated at an inside temperature of about 250° C. for 30 minutes. Evolution of hydrogen ceased in 30 minutes. Methanol (15 ml) was added to the reaction mixture, and the stabilized nickel was removed by filtration. The filtrate was distilled under reduced pressure to give 0.042 mole (7.0 g; yield 84 mole %) of a crude 1-acetylamino ethyl-2-methylimidazole fraction having a $bp_{20}$ of 223° to 233° C.

EXAMPLE 3

DETA (0.1 mole; 10.3 g) and 0.1 mole (10.2 g) of acetic acid were heated in a Claisen flask while evaporating water formed. The evaporation ceased in 1 hour, and the inside temperature finally reached about 250° C. During this time, 0.17 mole (3 ml) of water distilled out. Then, a bubble counter was fitted to the flask, and 5% by weight (1.1 g), based on the weight of the starting materials charged, of stabilized nickel was added to the reaction mixture obtained as above. The mixture was heated at an inside temperature of about 250° C. for 20 minutes. During this time, continuous evolution of hydrogen was observed.

After the reaction, 30 ml of methanol was added to the reaction mixture, and the stabilized nickel was separated by filtration. The filtrate was distilled under reduced pressure to give 0.072 mole (12.0 g; yield 72 mole % based on DETA) of a crude 1-acetylaminoethyl-2-methylimidazole fraction having a $bp_{20}$ of 220°–224° C.

EXAMPLE 4

DETA (0.1 mole; 10.3 g) and 0.2 mole (14.8 g) of propionic acid were heated for 1.5 hours as in Example 1. To the reaction mixture was added 1.1 g of stabilized nickel. The mixture was heated at an inside temperature of about 250° C. for 30 minutes. During this period, continuous evolution of hydrogen was observed.

After the hydrogen evolution ceased, about 30 ml of methanol was added to the reaction mixture. The stabilized nickel was removed by filtration, and the filtrate was distilled under reduced pressure to give 0.074 mole (14.3 g; yield 73.5 mole % based on DETA) of a crude 1-propionylaminoethyl-2-ethylimidazole fraction having a $bp_{20}$ of 218°–229° C.

The crude 1-propionylaminoethyl-2-ethylimidazole (0.074 mole; 14.3 g) obtained as above, 0.11 mole (4.4 g) of NaOH, 7 ml of ethylene glycol and 0.7 ml of water were heated under reflux at an inside temperature of 180° to 190° C. for about 1 hour. Then, 40 ml of ethanol was added, and the insoluble materials were separated by filtration. The filtrate was distilled under reduced pressure to give a fraction having a $bp_{10}$ of 135°–145° C. Oxalic acid was added to a methanol solution of the fraction, and the precipitated crystals were collected by filtration. An aqueous solution of sodium carbonate was added to the crystals to render them sufficiently alkaline and then they were dried. The dried product was extracted with ethanol. The extract was distilled under reduced pressure to give 0.04 mole (5.7 g; yield 41 mole % based on DETA) of 1-aminoethyl-2-ethylimidazole having a $bp_8$ of 140°–142° C.

EXAMPLE 5

DETA (0.1 mole; 10.3 g), 0.1 mole (5.5 g) of propionitrile and 0.2 g of sulfur were heated as in Example 2. In 2 hours, evolution of ammonia gas ceased, and the inside temperature finally reached about 180° C. The reaction mixture was distilled under reduced pressure to give a fraction having a $bp_{20}$ of 110°–137° C. Zinc dust (0.8 g) and one pellet of sodium hydroxide were added to the resulting fraction, and the mixture was heated with stirring at an inside temperature of 150° C. for 2 hours. The reaction mixture was extracted with methanol, and the extract was distilled under reduced pressure to give 0.083 mole (11.7 g; yield 82 mole % based on DETA) of a crude 1-aminoethyl-2-ethylimidazoline having a $bp_{20}$ of 115°–137° C.

The resulting imidazoline (0.05 mole; 7.1 g) and 0.05 mole (3.7 g) of propionic acid were heated in a Claisen flask while water formed was evaporated In about 1 hour, the evaporation ceased, and the inside temperature finally reached about 250° C. A bubble counter was then fitted to the flask, and 5% by weight (0.5 g), based on the weight of the starting materials charged, of stabilized nickel was added to the reaction mixture obtained as above. The mixture was heated at an inside temperature of about 250° C. for 40 minutes.

During this time, continuous evolution of hydrogen was observed. Methanol was added to the reaction mixture, and the stabilized nickel was separated by filtration. The filtrate was distilled under reduced pressure to give 0.033 mole (6.5 g; yield 66 mole % based on the imidazoline) of a crude 1-propionylaminoethyl-2-ethylimidazole fraction having a $bp_{20}$ of 221°–228° C.

EXAMPLE 6

DETA (0.1 mole; 10.3 g) and 0.2 mole (17.6 g) of isobutyric acid were heated for 1.5 hours as in Example 1. To the reaction mixture was added 1.4 g of stabilized nickel, and the mixture was heated at about 250° C. Evolution of hydrogen gas ceased in 40 minutes. Methanol (30 ml) was added to the reaction mixture, and the stabilized nickel was separated by filtration. The filtrate was distilled under reduced pressure to give 0.072 mole (16.0 g; yield 72 mole % based on DETA) of a crude 1-isobutyrylaminoethyl-2-isopropylimidazole fraction having a $bp_{20}$ of 218°–224° C.

A mixture composed of 0.072 mole (16.0 g) of the resulting crude fraction, 0.11 mole (4.4 g) of NaOH, 8 ml of ethylene glycol and 0.1 ml of water was heated under reflux for 1.5 hours. A sufficient amount of carbon dioxide gas was blown into the reaction mixture and 30 ml of methanol was added. The insoluble materials were separated by filtration. The filtrate was distilled under reduced pressure to give 0.039 mole (6.0 g; yield 39 mole % based on DETA) of a crude 1-aminoethyl-2-isopropylimidazole fraction having a $bp_{20}$ of 120°–139° C.

EXAMPLE 7

DETA (0.1 mole; 10.3 g) and 0.2 mole (40.1 g) of lauric acid were heated for 1 hour as in Example 1. To the reaction mixture was added 2.0 g of stabilized nickel, and the mixture was heated at an inside temperature of about 250° C. for 40 minutes. During this time, continuous evolution of hydrogen was observed. After evolution of hydrogen ceased, methanol was added to the reaction mixture. The stabilized nickel was separated by filtration, and the filtrate was concentrated under reduced pressure. The precipitated crude 1-laurylaminoethyl-2-undecylimidazole (m.p. 51°–57° C.) was collected in an amount of 0.084 mole (37.8 g; yield 84 mole % based on DETA) by filtration. A mixture composed of 0.084 mole (37.8 g) of the resulting imidazole compound, 32 ml of conc. sulfuric acid and 32 ml of water was heated under reflux for 4 hours, and made basic with aqueous ammonia. Then, 40 ml of ethanol was added. The aqueous layer was discarded, and the oil layer was separated and dried. The dried product was extracted with ethanol, and the extract was dried. The dried product was dissolved in methanol, and the solution was adjusted to pH 4 with oxalic acid. The precipitated crystals were collected by filtration, and dissolved in hot water. The resulting aqueous solution was neutralized with potassium carbonate and dried. The dried product was extracted with acetone, and the extract was dried to give 0.02 mole (5.2 g; yield 19 mole % based on DETA) of a crude 1-amino-ethyl-2-undecylimidazole.

EXAMPLE 8

DETA (0.1 mole; 10.3 g) and 0.2 mole (56.9 g) of stearic acid were heated for 1.5 hours as in Example 1. To the reaction mixture was added 3.4 g of stabilized nickel, and the mixture was heated at an inside temperature of about 250° C. for 1.5 hours. During this time, continuous evolution of hydrogen was observed. After the evolution of hydrogen ceased the reaction mixture was extracted with methanol using a Soxhlet extractor to separate the stabilized nickel. The extract was cooled and the precipitated crystals were collected by filtration. Recrystallization from methanol gave 0.085 mole (52.0 g; yield 85 mole % based on DETA) of the desired crude 1-stearoylaminoethyl-2-heptadecylimidazole.

A mixture composed of 0.085 mole (32.0 g) of the resulting crude product, 0.34 mole (13.5 g) of NaOH, 52 g of diethylene glycol and 1 g of water was heated at an inside temperature of about 180° C. for 3 hours, and then cooled. Then, 300 ml of water was added to the cooled mixture, and $H_3PO_4$ was added until the pH of the solution became 3.5. The precipitated crystals were collected by filtration. To the crystals was added 300 ml of hot methanol, and the insoluble materials were separated by hot filtration. The crystals precipitated from the filtrate was collected, and an aqueous solution of $Na_2CO_3$ was added to render the aqueous solution sufficiently basic. Then, it was dried under reduced pressure.

The dried product was extracted with acetone, and the extract was distilled under reduced pressure to give 0.04 mole (14.5 g; yield 42 mole % based on DETA) of the crude desired product 1-aminoethyl-2-heptadecylimidazole having a $bp_{20}$ of 130°–150° C. In its TLC (silica G, MeOH, color formation with B.T.B.), a tiny amount of the unreacted product was observed at an Rf of 0.0, and a large amount of the desired product, at an Rf of 0.35 to 0.45.

EXAMPLE 9

DETA (0.1 mole; 10.3 g) and 0.2 mole (24.4 g) of benzoic acid were heated for 1.5 hours as in Example 1. To the reaction mixture was added 1.8 g of stabilized nickel, and the mixture was heated at an inside temperature of about 250° C. for 2 hours. During this period, continuous evolution of hydrogen was observed. After the evolution of hydrogen ceased, about 50 ml of methanol was added to the reaction mixture. Then, the stabilized nickel was removed by filtration, and the filtrate was distilled under reduced pressure to give 0.056 mole (16.3 g; yield 56 mole % based on DETA) of a crude 1-benzoyl-aminoethyl-2-phenylimidazole fraction having a $bp_3$ of 168°–246° C. On standing, this fraction solidified to neutral crystals having a melting point of 114° to 119° C.

A mixture composed of 0.056 mole (16.3 g) of the crude 1-benzoylaminoethyl-2-phenylimidazole, 0.1 mole (4.0 g) of NaOH, 8 ml of ethylene glycol and 0.1 ml of water was heated at an inside temperature of 170° to 190° C. for about 1 hour, and then cooled. Ethanol (about 50 ml) was added, and the mixture was heated. The insoluble materials were separated by filtration, and the filtrate was distilled under reduced pressure to give 0.029 mole (5.5 g; yield 29 mole % based on DETA) of a crude 1-aminoethyl-2-phenylimidazole fraction having a $bp_{20}$ of 162°–196° C.

EXAMPLE 10

DETA (0.1 mole; 10.3 g), 0.1 mole (10.3 g) of benzonitrile and 0.2 g (2% by weight based on DETA) of sulfur were heated as in Example 2. In 2.5 hours, evolution of ammonia gas ceased, and the inside temperature finally reached 180° C. Then, 0.8 g (2 moles per mole of sulfur) of zinc dust was added to the reaction mixture, and the mixture was heated at an inside temperature of 150° C. for 2 hours. After the reaction mixture was allowed to cool, it was extracted with methanol. The extract was distilled under reduced pressure to give 0.078 mole (14.7 g; yield 78 mole %) of a crude 1-aminoethyl-2-phenylimidazoline fraction having a $bp_{20}$ of 200°–204° C.

The crude 1-aminoethyl-2-phenylimidazoline (0.1 mole; 18.9 g) obtained as above and 0.1 mole (12.2 g) of benzoic acid were heated in a Claisen flask while the water formed was evaporated. In 1.5 hours, the evaporation ceased, and the inside temperature finally reached about 250° C. During this period, 0.083 mole (1.5 ml) of water distilled out.

A bubble counter was then fitted to the flask, and 3% by weight (1.0 g) based on the weight of the starting materials charged, of stabilized nickel was added to the reaction mixture obtained as above. The mixture was heated at an inside temperature of about 250° C. for 1.5 hours. During this time, continuous evolution of hydrogen was observed. After the evolution of hydrogen ceased, about 50 ml of methanol was added to the reaction mixture. The stabilized nickel was separated by filtration, and the filtrate was distilled under reduced pressure to give 0.062 mole (18.2 g; yield 62 mole %) of a crude 1-benzoylaminoethyl-2-phenylimidazole having a $bp_3$ of 201°–245° C. On standing, this fraction solidified and showed a melting point of 114°–119° C.

EXAMPLE 11

DETA (0.1 mole; 10.3 g) and 0.2 mole (12.0 g) of acetic acid was heated in a Claisen flask while the water formed was evaporated. In 1.5 hours, the evaporation ceased, and the inside temperature finally reached about 250° C. After the flask was allowed to cool, the reaction mixture was taken out. It was used as a starting material for dehydrogenation reaction, and 5% by weight of developed Raney cobalt, 2% by weight, calculated as metal, of 10% platinum asbestos and 0.02% by weight, calculated as metal, of 5% palladium activated carbon were added respectively to it. The mixture was heated at 250° C. for 2 hours, and the evolution of hydrogen was examined. With all these three metal catalysts, hydrogen evolution was observed, but the rates of evolution were lower than in the case of stabilized nickel. It was determined by TLC that the reaction mixture in each case contained 1-acetylaminoethyl-2-methylimidazole as a main component.

EXAMPLE 12

One hundred parts by weight of a liquid epoxy resin (Epikote #828; a diglycidyl ether of bisphenol A made by Yuka Shell Epoxy Co., Ltd.) was mixed with each of the imidazole compounds indicated in the following table in the amounts indicated. The following table shows the viscosities, gel times and pot lives of the resulting mixtures.

| Imidazole compound | | | | |
|---|---|---|---|---|
| 1-aminoethyl-2-methylimidazole | Amount | 2 | 4 | 8 |
| | Viscosity (poise) | 103 | — | — |
| | Gel time | 1'29" | 48" | 28" |
| | Pot life | 8 hours | — | — |
| 1-aminoethyl-2-ethylimidazole | Amount | 2.2 | 4.5 | 8.9 |
| | Viscosity (poise) | 110 | — | — |
| | Gel time | 4'24" | 1'34" | 58" |
| | Pot life | 1 days | — | — |
| 1-aminoethyl-2-phenylimidazole | Amount | 3.0 | 6.0 | 12.0 |
| | Viscosity (poise) | 120 | — | — |
| | Gel time | 9'17" | 3'32" | 1'50" |
| | Pot life | 3 day | — | — |
| 1-aminoethyl-2-undecylimidazole | Amount | 4.2 | 8.5 | 16.5 |
| | Viscosity (poise) | 135 | — | — |
| | Gel time | 3'46" | 1'43" | 50" |
| | Pot life | 1 day | — | — |
| 1-aminoethyl-2-heptadecyl-imidazole | Amount | — | 11.2 | 22.4 |
| | Viscosity (poise) | — | — | — |
| | Gel time | — | 1'56" | 1'19" |
| | Pot life | — | 1 day | 1 day |

The amounts were in parts by weight, and the indicated amounts in each column are equimolar to each other. In other words, as the molecular weight increases, the amount increases proportionally.

About 0.3 g of each mixture was placed on a hot plate kept at a temperature of 150° C., and spread thin with a metallic spatula. The time which lapsed until there was no roping between the mixture and the spatula is defined as the gel time.

The mixture was stored at 25° C., and the time which elapsed until its viscosity reached a value twice the initial value is defined as the pot life.

EXAMPLE 13

One hundred parts by weight of the same liquid epoxy resin (Epikota #828) as used in Example 12 was mixed with 2 parts by weight of 1-aminoethyl-2-methylimidazole. The mixture was heated at 75° C. for 2 hours and then at 150° C. for 4 hours to cure it. The mechanical and electrical properties of the cured product are shown below.
1. Glass transition temperature (TMA method): 162° C.
2. Heat distortion temperature: 163° C.
3. Coefficient of linear expansion: $90 \times 10^{-6}$ deg$^{-1}$
4. Flexural strength: 7.2 kg/mm$^2$ at 25° C.
   3.3 kg/mm$^2$ at 150° C.
5. Flexural modulus: 290 kg/mm$^2$ at 25° C.
   100 kg/mm$^2$ at 150° C.
6. Water absorption after boiling
   (4 hours later): 0.46% by weight
7. Volume resistivity: $2.01 \times 10^{15}$ ohms-cm at 25° C.
   $2.85 \times 10^{11}$ ohms-cm at 150° C.
8. Dielectric constant
   3.4 at 25° C. and 60 Hz
   3.9 at 150° C. and 60 Hz
   3.9 at 25° C. and 1 KHz
   3.6 at 150° C. and 1 KHz
9. Dielectric tangent
   0.54% at 25° C. and 60 Hz
   30% at 150° C. and 60 Hz
   0.91% at 25° C. and 1 KHz
   2.7% at 150° C. and 1 KHz The above properties are nearly equivalent to those of a cured product of the epoxy resin obtained by using 2E4MZ instead of 1-aminoethyl-2-methylimidazole.

EXAMPLE 14

One hundred parts by weight of the same epoxy resin (Epikote #828) as used in Example 12 was mixed with 87.4 parts by weight of methyltetrahydrophthalic anhydride (Epiclon BS70, a tradename for a product of Dainippon Ink and Chemicals, Inc.) and 0.2 parts by weight of 1-aminoethyl-2-methylimidazole. The mixture was heated at 120° C. for 2 hours and then at 150° C. for 4 hours to cure it. The mechanical and electrical properties of the cured product are shown below.
1. Glass transition temperature (TMA method): 150° C.
2. Coefficient of linear expansion: $77 \times 10^{-6}$ deg$^{-1}$
3. Flexural strength: 16.6 kg/mm$^2$ at 25°
   4.2 kg/mm$^2$ at 130° C.
4. Flexural modulus: 340 kg/mm$^2$ at 25° C.
   190 kg/mm$^2$ at 130° C.
5. Water absorption after boiling (after 4 hours):
   0.36 wt.%
6. Volume resistivity: $2.3 \times 10^{16}$ ohms-cm at 25° C.
   $3.2 \times 10^{13}$ ohms-cm at 130° C.
7. Dielectric constant
   3.0 at 25° C. and 60 Hz
   3.1 at 130° C. and 60 Hz
   3.0 at 25° C. and 1 KHz
   3.1 at 130° C. and 1 KHz
8. Dielectric tangent
   0.82% at 25° C. and 60 Hz
   5.8% at 130° C. and 60 Hz
   0.76% at 25° C. and 1 KHz
   0.40% at 130° C. and 1 KHz The above properties are nearly equivalent to those of a cured product of the epoxy resin obtained by using 2E4MZ instead of 1-aminoethyl-2-methylimidazole.

EXAMPLE 15

One hundred parts by weight of a solid epoxy resin (Epikote #1001, a diglycidyl ether of bisphenol A produced by Yuka Shell Epoxy Co., Ltd.) was dissolved in 33.3 parts by weight of ethyl methyl ketone. The solution was mixed with a solution of 4 parts by weight of dicyandiamide and 0.2 parts by weight of 1-aminoethyl-2-methylimidazole in 45.8 parts by weight of methyl Cellosolve as a curing agent to form a mixed solution. The mixed solution was impregnated in a glass cloth having a size of about 5 cm×30 cm. The impregnated cloth was then dried to remove the solvent and thus to form a prepreg.

The prepreg had a storage stability at room temperature of 9 hours, and a gel time, measured on a hot plate at 150° C., of 4 minutes and 15 seconds.

What we claim is:

1. A process for producing a 1-aminoethyl-imidazole compound represented by the general formula

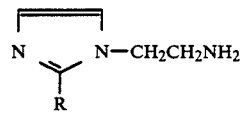

wherein R is an alkyl or phenyl group, which comprises hydrolyzing a 1-acylaminoethyl-imidazole compound represented by the general formula

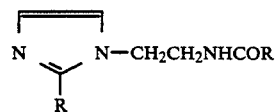

wherein R is as defined.

2. The process of claim 1 wherein the hydrolysis is carried out in a solvent selected from the group consisting of water, hydrous ethylene glycol and hydrous diethylene glycol in the presence of an alkali hydroxide or sulfuric acid.

* * * * *

UNITED STATES PATENT AND TRADEMARK OFFICE
CERTIFICATE OF CORRECTION

PATENT NO. : 4,826,991
DATED : May 2, 1989
INVENTOR(S) : NATSUO SAWA, ET AL.

It is certified that error appears in the above-identified patent and that said Letters Patent is hereby corrected as shown below:

On the face of the patent, under "ABSTRACT", line 3, delete " 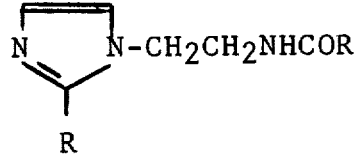 ", insert -- 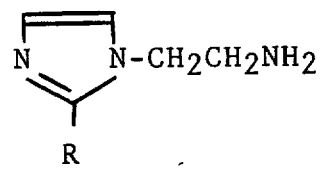 --.

Signed and Sealed this

Sixth Day of February, 1990

Attest:

JEFFREY M. SAMUELS

Attesting Officer    Acting Commissioner of Patents and Trademarks